United States Patent
Wolf et al.

(12) 
(10) Patent No.: US 6,228,402 B1
(45) Date of Patent: *May 8, 2001

(54) XYLITOL-CONTAINING NON-HUMAN FOODSTUFF AND METHOD

(75) Inventors: Phyllis Wolf, Mt Prospect, IL (US); John Peldyak, Mt. Pleasant, MI (US)

(73) Assignee: Adore-A-Pet, Ltd., Mount Prospect, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/685,268

(22) Filed: Oct. 10, 2000

Related U.S. Application Data

(62) Division of application No. 09/346,822, filed on Jul. 2, 1999, now Pat. No. 6,159,508, which is a continuation of application No. 08/767,001, filed on Dec. 19, 1996, now Pat. No. 5,989,604.

(51) Int. Cl.$^7$ ..................................................... A23L 1/236
(52) U.S. Cl. .......................... 426/94; 426/103; 426/548; 426/805
(58) Field of Search .............................. 426/94, 103, 548, 426/805

(56) References Cited

U.S. PATENT DOCUMENTS

| | | | | |
|---|---|---|---|---|
| 4,518,581 | * | 5/1985 | Miyake et al. ........................ | 424/48 |
| 5,000,943 | * | 3/1991 | Scaglione et al. .................... | 424/57 |
| 5,015,485 | * | 5/1991 | Scaglione et al. .................... | 426/94 |
| 5,114,704 | * | 5/1992 | Spania et al. ........................ | 424/57 |
| 5,405,836 | * | 4/1995 | Richar et al. ........................ | 514/23 |

* cited by examiner

*Primary Examiner*—Chhaya D. Sayala
(74) *Attorney, Agent, or Firm*—Ryndak & Suri

(57) ABSTRACT

A pet foodstuff and treatment method for reducing the incidence of dental caries in non-human animals is provided. The treatment method includes orally administering the xylitol by allowing the pet to consume the xylitol-containing foodstuff in an effective amount. The pet foodstuff is composed of an effective amount of xylitol and an edible pet food. The xylitol may be present as a coating or in bulk.

7 Claims, 2 Drawing Sheets

XYLITOL-CONTAINING NON-HUMAN FOODSTUFF AND METHOD

CROSS REFERENCE TO RELATED APPLICATIONS

This is a divisional of U.S. patent application Ser. No. 09/346,822, filed Jul. 2, 1999, now U.S. Pat. No. 6,159,508, issued Dec. 12, 2000, which is a continuation of U.S. patent application Ser. No. 08/767,001, filed Dec. 19, 1996, now U.S. Pat. No. 5,989,604, issued Nov. 23, 1999.

FIELD OF THE INVENTION

The invention relates to edible pet foodstuff for dental caries prevention. The invention also relates to a process of preparing such edible pet foodstuff.

BACKGROUND OF THE INVENTION

Dental plaque acids, produced by *Streptococcus mutans* and other acidogenic bacteria in an animal's mouth, are responsible for the formation and exacerbation of dental caries and the occurrence of malodorous breath in animals.

It is believed that recently dental caries and malodorous breath have become more prevalent in pets. While not wishing to be bound by theory, it is believed that certain additives or materials in pet food may be responsible at least in part.

A need exists for a pet foodstuff and a treatment method for treating pet's gums and teeth to reduce the incidence of caries and to control malodorous breath in pets.

SUMMARY OF THE INVENTION

In accordance with the present invention, it has been discovered that the incidence of caries in pets can be reduced by placing xylitol in contact with a pet's gums and teeth.

In one aspect, this invention provides a range of materials containing various xylitol mixtures to place the xylitol into contact with an animal's teeth for the longest period of time possible. By doing so, xylitol reduces dental plaque acids and inhibits the growth of *S. mutans*, and other acidogenic bacteria responsible for the formation and exacerbation of dental caries in dogs, cats, horses, pets and other show animals. Another objective is to provide a dry biscuit or treat type of food that synergistically operates with the xylitol to lessen the incidence of dental plaque or tartar by chewing the dry biscuit material.

In accordance with another aspect of the invention, a process is provided for preparing dry, solid animal food in biscuit or treat form with a topical additive onto which the xylitol combination is sprayed, brushed or dipped thereby permitting the topical coating to remain on the outside of the biscuit or treat but firmly adhered thereto. This will increase the time the xylitol combination is placed in direct contact with the animal's teeth increasing the time xylitol will affect any *S. mutans* present in the mouth. Another objective of the invention is to provide a means of controlling malodorous breath, especially in dogs and cats, by increasing salivation. Another objective of the invention is to prepare a xylitol-containing gel that can be placed directly onto the animal's teeth. A further objective of this invention is to provide a powder to be placed in the animal's drinking water to provide further protection from plaque acids by increasing the contact of xylitol with the animal's teeth over the period of a day. This is especially important for "free feeders," that is, animals which continuously feed throughout the day and are not amenable to being fed the xylitol-containing biscuits after scheduled meals.

In accordance with still another aspect of the invention, a process is provided of preparing a chew rawhide with a topically applied and/or impregnated xylitol-containing mixture. The goal is to maximize exposure during the day of the xylitol-containing mixture to be in direct contact with the animal's teeth.

All of the above applications of the invention taken together further describe another aspect of the invention, that is, this is a comprehensive delivery system of placing xylitol in contact with the animal's teeth for the greatest period of time during the day.

In one aspect, the invention permits the use of a comprehensive method of exposing the animal's teeth to the xylitol product. As stated above, this is accomplished using a variety of delivery materials, that is, topically coated biscuits and treats, topically coated or impregnated rawhide chew bones or toys, "sandwich" style or "pocket" biscuits or treats, a powder soluble in water, and a topical gel application.

The "sandwich" or "pocket" style biscuits or treats are made in such a way that the xylitol mixture is layered using a special process between flat biscuits to create a biscuit that serves a dual purpose of reducing tartar or plaque by the action of chewing against the teeth, and to release the xylitol mixture slowly after the "chewing" action is accomplished.

In one aspect of the invention, novel dog biscuits and cat treats are provided. The farinaceous-based baked biscuits have certain constituents including xylitol suitable for animal consumption, generally food grade xylitol. Xylitol exhibits therapeutic properties for the amelioration of dental caries and conditions promoting the formation of dental caries. A suitable adherence material, such as gum arabic (or other suitable vegetable gum) may be present as a separate coating or in a mixture with the xylitol, for example. When used as a separate coating, the gum arabic is applied to the surface of the biscuit or treat and is allowed to dry or as otherwise required for that particular type of adherent material. This improves the adherence of the xylitol compound to the surface of the biscuit or treat for greater effectiveness. More than one coating layer may be used. The amount of xylitol in such coating should approximate one-half gram per biscuit. Generally, the xylitol will be applied to the surface of the biscuit (or treat) after preparation of the biscuit is otherwise completed. When the coated biscuit is consumed by the animal, release of the xylitol product into the animal's mouth and on the teeth is maintained for the longest time. Xylitol added to the bulk dough before the baking process can be done, but is not preferred because it does not place the maximum amount of xylitol in direct contact with the animal's teeth, a process important to maximize effectiveness.

Another aspect of the invention involves the use of chew toys and bones or treats. These chew toys are made of rawhide, pigskin (in the form of "roll-ups") or other suitable material and are either coated with or impregnated with a xylitol mixture.

Another aspect of the invention involves the use of a water soluble consumable mouthwash powder mix with xylitol in combination with other suitable materials such as aloe vera concentrate and/or zinc amino acid chelate designed to be placed into a pet's water bowl to provide continuous xylitol contact every time the animal drinks water.

Another aspect of the invention involves the use of a topical gel containing a xylitol, lactitol, and HSH (hydrogenated starch hydrolyzate syrup) mixture. This is applied directly to an animal's teeth especially during periods when the animal is not likely to be fed.

The term "dog biscuit" as used herein means a biscuit for a dog that is baked or otherwise processed to form a biscuit. These dog biscuits can be made from any suitable dough or other starting material. One such advantageous combination is a biscuit made from a dough consisting of whole wheat flour, brewer's yeast, wheat germ, edible bone meal, chicken broth, canola oil, and whole egg. There is a deliberate method to using only natural ingredients in these formulations. Added sugar, corn syrup, any sucrose or fructose product is completely avoided as that could compromise the efficacy of the cariostatic and anti-cariogenic effects of the xylitol compound as described herein.

The term "cat treat" or treat as used herein means a treat for a cat that is baked or otherwise processed to form a treat. These cat treats can be made from any suitable dough or other starting material. One such advantageous combination consists of barley flour, ground chicken, whole eggs, edible bone meal, rye flour, canola oil, wheat germ, ascorbic acid, taurine, water, chicken or beef broth.

The term "sandwich" as used herein means a pet foodstuff which is comprised of two biscuits, treats, or other bulk foodstuff which are joined with a xylitol mixture between the biscuits, treats or other foodstuff.

The term "pocket" as used herein means a pet foodstuff which contains a xylitol mixture in the center of the pet foodstuff wherein the body of such pet foodstuff has been folded over and sealed to encompass the xylitol center.

The invention compositions of xylitol and xylitol-containing mixtures ameliorate the condition of dental caries and malodorous breath in animals, help heal inflamed gums, and otherwise re-mineralize teeth in which the formation of dental caries is incipient. As used in combination of biscuits or treats, powder added to drinking water, chew toys, freeze dried organ treats (e.g. liver, kidney, dried muscle chew treats, and gel, all of the products described herein comprise a comprehensive delivery system of xylitol and contribute to the dental health and well-being of animals using the invention. These "xylitol delivery systems" for pets can incorporate other ingredients that promote the health of hard and soft dental tissues. Examples of these ingredients are: zinc compound, parsley, and baking soda (dental malodor control), bone meal (supplies calcium and phosphate ions which promotes re-mineralization of teeth), Coenzyme Q10 (promotes periodontal health), folic acid (vitamin), the following botanicals: aloe vera, comfrey, rosemary, goldenseal, horsetail, arnica, calendula, barley grass, chamomile, bloodroot, siwak-miswak, pullulan, horse chestnut, neem, peelu, propolis, green tea, myrrh, birch bark, white oak bark, tea tree oil, grape seed extract and wheat germ, and the following enzymes: bromelain, papain and quercetin.

DETAILED DESCRIPTION OF THE INVENTION

Figure 1:
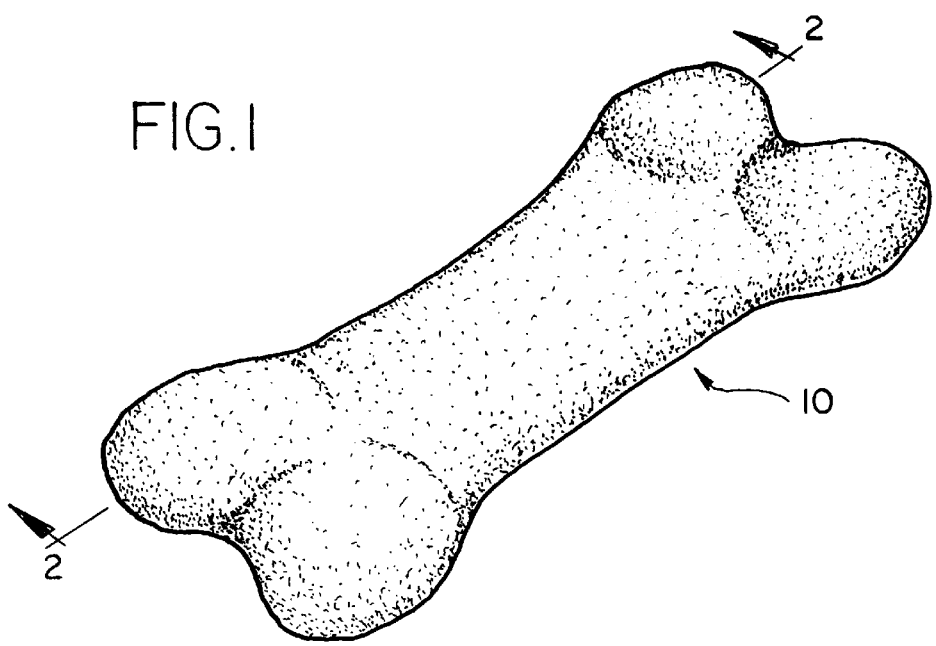
FIG. 1 is a perspective view of a xylitol-coated dog biscuit.

All parts, percentages, ratios and proportions are set forth on a weight basis in grams unless otherwise stated or otherwise obvious to one skilled in the art. As used herein, all temperatures are in degrees Fahrenheit unless otherwise stated herein or otherwise obvious to one skilled in the art.

If desired, specific breath freshening agents may be added to any of the biscuits and treats. Agents such as zinc amino acid chelate, parsley (chlorophyll source) and baking soda may be used for breath freshening.

A. Preparation of the Material

1. Biscuits and Treats

The dog biscuits and cat treats must themselves be thoroughly dry after baking. The dog biscuits and cat treats are prepared by brushing, spraying or dipping each of the biscuits or treats with a xylitol and gum arabic mixture to coat the material. All such products are thoroughly dried either by heat or evaporation in a humidity controlled environment. The gum arabic and xylitol mixture gives the product a coating permitting the xylitol a greater ability to adhere to the outside of the biscuit or treat without penetrating or affecting the underlying material. Xylitol should comprise between 0.25% and 2.5% by weight of the total biscuit or treat. If a coating is utilized, the coating preferably should be between approximately 0.01 and 0.1 inches thick. The objective is to separate the xylitol compound from the biscuit or treat so that both may work independently, that is, chewing the treat will tend to scrape at built up plaque or tartar while the separate coating of xylitol will come into maximum contact with the animal's teeth to control *S. mutans*, bathe the gums, and aid in re-mineralization of certain dental caries.

2. Sandwich Biscuits/Treats and Pocket Biscuits

In sandwich or pocket biscuits or treats, xylitol should be present in an amount from about 0.25% to 2.5% by total weight of the item.

a. Sandwich Biscuits/Treats for Dogs and Cats

Preferably, sandwich biscuits/treats for dogs and cats are generally flat, although they can be of any desired shape and usually are composed of two opposed outer biscuit/treat pieces, usually labeled, and joined together with a xylitol-containing layer "sandwiched" between the two flat layers, appearing much the same as a cookie with a cream filling. This filling or layer can be the same for both dogs and cats and consists of, for example: powdered or granulated food grade xylitol, gum arabic, beef broth, chicken broth or distilled water, lecithin, Coenzyme Q10, folic acid, aloe vera, comfrey, rosemary, goldenseal, horsetail, arnica, calendula, barley grass, chamomile, bloodroot, siwak-miswak, pullulan, horse chestnut, neem, peelu, propolis, green tea, myrrh, birch bark, white oak bark, tea tree oil, grape seed extract, wheat germ, bromelain, papain and quercetin. If necessary, water may be added as a diluant. The xylitol-containing layer should contain material for maintaining the outer biscuit/treat layers together.

The sandwich biscuit for dogs usually will be made from a dough. Preferably the dough will contain all-natural ingredients and can include whole wheat flour, buckwheat, brewer's yeast, wheat germ, corn meal, edible bone meal, chicken broth, canola oil, and whole egg. The flours used (e.g., whole wheat, barley, soy, corn, rye, buckwheat, potato, rice, etc.) can be varied to accommodate allergic reactions the pet may have to one or more of the above ingredients. Any suitable dough composition can be utilized. In one embodiment, the sandwich treat for cats consists of dough containing all-natural ingredients: one or more flours (e.g., barley, whole wheat flour, corn meal, rye flour, soy flour, etc.), ground chicken, whole eggs, edible bone meal, canola oil, wheat germ, ascorbic acid, taurine, water, chicken or beef broth. The combination of flour may consist of one or more of the specified flours depending on the allergic reaction of the animal. Other flour combinations or a single flour ingredient may be substituted. The dough mixture for either biscuits or treats is rolled flat or otherwise formed into a flat sheet and may be cut into assorted shapes and sizes. It is preferable that the portion of the sheets that will be opposed in the sandwich are flat to allow the xylitol-containing layer to be of uniform thickness in the finished sandwich. The individual cut shapes are suitably baked, such as at approximately 300 degrees for approximately 45 minutes and are allowed to thoroughly cool to room temperature. As is known in the art, the optimum baking temperature and time will depend on various factors, including dough composition and thickness, for example. Then the xylitol-containing layer or filling as stated above is applied in a suitable manner, such as by spreading, for example, on at least one of the two biscuit/treat layers making up the biscuit/treat. A top biscuit/treat layer is applied on top of and preferably in substantial registry with the bottom layer with the xylitol-containing layer or filling located between the two biscuit/treat layers. If desired the top and bottom biscuit/treat layers can be of the same or different size and shape. Optionally, the assembled biscuits/treats can be dried in a humidity controlled environment at room temperature (68 to 80 degrees) for at least eight (8) hours until thoroughly dry.

b. Pocket Biscuits

Using a biscuit dough or cat treat dough, the dough is rolled or otherwise formed into a sheet and while still wet the following ingredients are added: powdered xylitol, powdered lactitol and aloe vera. The dough is then folded in half and cut into assorted shapes crimping the edges (other than the fold edge when present) of each of the shapes to form a closed pocket and then suitably baked, such as at approximately 300 degrees for approximately 45 minutes. As is known in the art, the optimum baking temperature and time will depend on various factors, including dough composition and thickness, for example. During the baking process the powdered ingredients melt inside the two layers of dough forming a somewhat "sticky" or "tacky" substance that will adhere to the dog's or cat's teeth when they chew the biscuit maximizing the delivery of xylitol to the teeth and gums. Preferably, when fully baked, the ingredients within the pocket remain "sticky" or "tacky" at the time of consumption by a pet.

3. Chews, Bones, Rawhides and Pigskins

Preferably, chews, bones, rawhides and pigskins contain at least about 0.25% xylitol by total weight of the item.

One suitable preferred method is hereinafter described. The pigskin is preferably a flat sheet. One side of the pigskin is coated with powdered xylitol and powdered lactitol. The coated pigskin is heated to make it pliable and is rolled or otherwise formed into a tubular shape. It is then cooled, usually to room temperature to retain its tubular shape. If desired, the pigskin may be cut into smaller sizes.

Alternatively, a mixture of xylitol, lactitol and HSH (hydrogenated starch hydrolyzate syrup) is heated to form a uniform solution. The resulting solution is applied to preferably one side of the pigskin. The coated pigskin is heated to make it pliable and is rolled or otherwise formed into a tubular shape. It is then cooled, usually to room temperature to retain its tubular shape. If desired, the pigskin may be cut into smaller sizes.

For the bones, the same ingredients are used as those for the pigskin. The ingredients are heated to form a solution and are introduced into the bone cavity by any suitable method, including brushing or spraying, and are allowed to cool.

For rawhides, preferably a flat sheet is utilized. Preferably one side of the rawhide is coated with powdered xylitol, powdered lactitol and HSH (hydrogenated starch hydrolyzate syrup). This rawhide is heated to make it pliable and is rolled or otherwise formed into a tubular shape. It is then cooled, usually to room temperature to retain its tubular shape. If desired, the rawhide may be cut into smaller sizes.

Alternatively, a mixture of xylitol, lactitol and HSH (hydrogenated starch hydrolyzate syrup) is heated to form a uniform solution. The resulting solution is applied to preferably one side of the pigskin. The coated pigskin is heated to make it pliable and is rolled or otherwise formed into a tubular shape. It is then cooled, usually to room temperature to retain its tubular shape. If desired, the pigskin may be cut into smaller sizes.

For chews (chew toys, freeze dried organ treats (e.g., liver, kidney, dried muscle chew treats), a xylitol mixture can be made with any number of compounds, such as xylitol and lactitol and sprayed, brushed or dipped onto the chew toy.

4. Xylitol Powdered Consumable Mouthwash

Consistent with a comprehensive dental delivery system and in an effort to make the xylitol product available to the animal as frequently as possible, one gram of xylitol is placed into a pet's water bowl to keep xylitol available for distribution to the pet's mouth, teeth and gums. This powder may be in granular or powdered form but must consist of food grade xylitol.

Additionally other ingredients (either singly or in combination) may be added such as aloe vera, zinc amino acid chelate, baking soda or various botanicals or enzymes.

A typical formulation for a single serving per cup of water consists of a range of 2 grams to 4 grams of xylitol, 25 to 75 milligrams of aloe vera (a 200:1 concentrate), 1 to 5 milligrams of zinc amino acid chelate. Optionally, 1 to 5 milligrams of baking soda and flavorings may be added.

5. Xylitol Gel

Three separate xylitol formulae may be used for the Xylitol Gel Product as follows:

(1) Xylitol and lactitol heated together to form a gel. The amounts are to be determined by a ratio of at least 51% xylitol and the balance is made up of lactitol. (Xylitol at least 51% and lactitol).

(2) Xylitol, lactitol and HSH (hydrogenated starch hydrolyzate syrup) are heated together. Typical proportions are Xylitol fifty percent (50%), Lactitol thirty percent (30%), and HSH twenty percent (20%).

(3) Xylitol and HSH are heated together. Typical proportions must include at least fifty one (51%) percent xylitol and the balance is lactitol.

C. Method of Administration

Delivery of xylitol-containing mixture is preferably made as follows:

(1) Feeding a dog biscuit or cat treat immediately after the animal is fed a regularly scheduled meal.

(2) Use of xylitol powder in the animal's water allowing the animal access to some concentration of xylitol throughout the day or if the animal is allowed to "free feed" which means that it has "on demand" feeding as it desires.

(3) Use of chew toys or treats either coated or impregnated with the xylitol mixture. This places xylitol in contact with teeth and gums during the period of use.

(4) Application of a topical gel containing xylitol with lactitol and/or HSH which "sticks" to the animal's teeth and gradually bathes the gums during the night or during times when the animal is not likely to feed or drink.

D. Effectiveness and Use

Xylitol and xylitol-containing compounds have been the subject of extensive studies. For best results, from about 0.5 to 5 grams of xylitol in total should be consumed daily by dogs, and from about 0.25 to 3 grams of xylitol in total should be consumed by cats.

Figure 2:
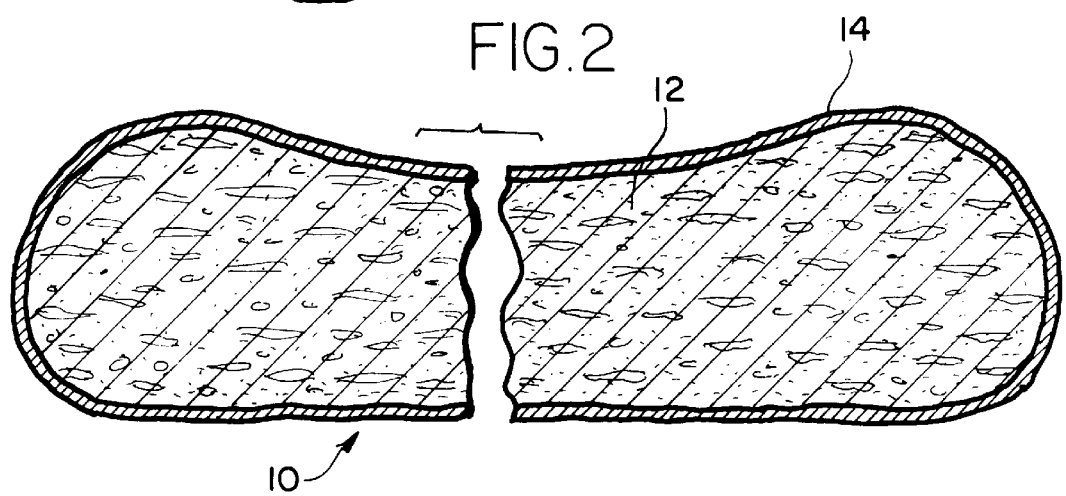
FIG. 2 is a cross-sectional view of the biscuit of FIG. 1 taken along line 2—2 of FIG. 1.

Referring to the figures generally, and particularly to FIGS. 1 and 2, there is illustrated a pet foodstuff 10 which in this case is a dog biscuit, in accordance with the invention. Pet foodstuff 10 is composed of a solid body 12 of baked farinaceous material and xylitol solid coating 14. Body 12 can be formed by any suitable method and can be composed of any conventional dog biscuit. For example, body 12 of pet foodstuff 10 can be made from the formulae set forth in Tables I and II which are disclosed for illustrative purposes only, not as a limitation on the present invention.

The present product can be made by any suitable method, such as by first cooking a pet foodstuff with the following ingredients, and then applying a coating containing an effective amount of xylitol.

TABLE I

Dog Biscuits

| | |
|---|---|
| 2 Cups Whole Wheat Flour (or other suitable flour) | 250 to 400 grams |
| ½ Cup Buckwheat, rye or a barley flour | 40 to 70 grams |
| ½ Cup Brewer's Yeast | 30 to 50 grams |
| 1 Cup Wheat Germ | 80 to 110 grams |
| ½ Cup Corn Meal, Potato, Rice or Soy Flour | 40 to 70 grams |
| ½ Cup Parsley Flakes | 0.3 to 0.7 grams |
| ¼ teaspoon edible bone meal | 0.5 to 1.2 grams |
| 1¼ Cup Distilled Water, Beef or Chicken Broth | 200 to 300 grams |
| ½ Cup of Canola, Olive or Sunflower Oil | 70 to 100 grams |
| ¼ Cup of Sunflower or Pumpkin Seeds | 20 to 40 grams |
| 1 Whole Egg | 40 to 60 grams |
| Powdered Xylitol | 3 to 7 grams |
| Lecithin | 0.75 to 1.25 grams |
| aloe vera | 0.3 to 0.7 grams |
| Coenzyme Q10 | 50 to 150 milligrams |
| Grape Seed Extract | 0.3 to 0.7 grams |

TABLE II

Cat Treats

| | |
|---|---|
| 2 Cups Barley or Whole Wheat Flour | 250 to 400 grams |
| Ground Chicken | 75 to 100 grams |
| 2 Whole Eggs | 80 to 120 grams |
| ⅛ teaspoon edible bone meal | 0.25 to 0.7 grams |
| ½ Cup Corn Meal | 40 to 70 grams |
| ½ Cup Rye or Soy Flour | 250 to 400 grams |
| ½ Cup Canola Oil | 70 to 100 grams |
| ½ Cup Wheat Germ | 40 to 55 grams |
| Ascorbic Acid | 0.5 gram |
| Taurine | 0.5 gram |
| 1¼ Cups Distilled Water, Chicken or Beef Broth | 200 to 300 grams |
| Powdered Xylitol | 3 to 7 grams |

TABLE II-continued

Cat Treats

| | |
|---|---|
| Lecithin | 0.75 to 1.25 grams |
| aloe vera | 0.3 to 0.7 grams |
| Coenzyme Q10 | 50 to 150 milligrams |
| Grape Seed Extract | 0.3 to 0.7 grams |

Figure 3:
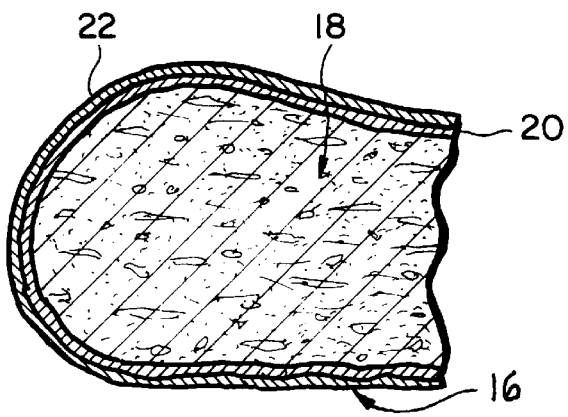
FIG. 3 is a cross-sectional view of an alternative embodiment of the biscuit with two layers of xylitol coating.

Referring to FIG. 3, there is illustrated another pet foodstuff 16, in accordance with the present invention. Pet foodstuff 16 is in the form of a dog biscuit which is composed of a body 18, an adherent coating 20 and a xylitol-containing coating 22. Body 18 can be produced in a manner similar to that used to produce body 12 of FIGS. 1 and 2. Adherent coating 20 is provided to improve the adherence of xylitol-containing coating 22 to body 18. Adherent coating 20 is comprised of a vegetable gum (or other suitable material), which has been applied to body 18 by brushing, spraying, dipping or any other method known by those skilled in the art, and suitably dried. Any material that provides the desired adherence for coating 22 can be utilized provided such material does not produce any unwanted effect or is otherwise not suitable for ingestion by a pet.

Figure 4:
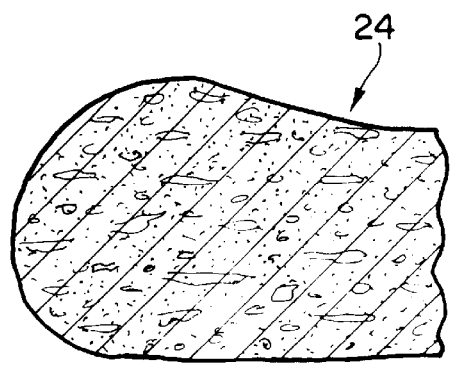
FIG. 4 is a cross-sectional view of an alternative embodiment of the biscuit without a xylitol coating.

Reference to FIG. 4 illustrates another embodiment of the present invention, which is a pet foodstuff 24. Pet foodstuff 24 can be produced in a manner similar to that used to produce body 12 and contains xylitol dispersed throughout the bulk.

Xylitol-containing coating 14 is composed of xylitol and can be made as follows:

E. Xylitol Coating or Filling Mixture

The Xylitol Coating mixture is to be used with the above biscuits and treats and consists of seventy-five (75) to one hundred fifty (150) grams of xylitol, five (5) to fifteen (15) grams of gum arabic, and ten (10) to twenty-five (25) grams of water.

Figure 5:
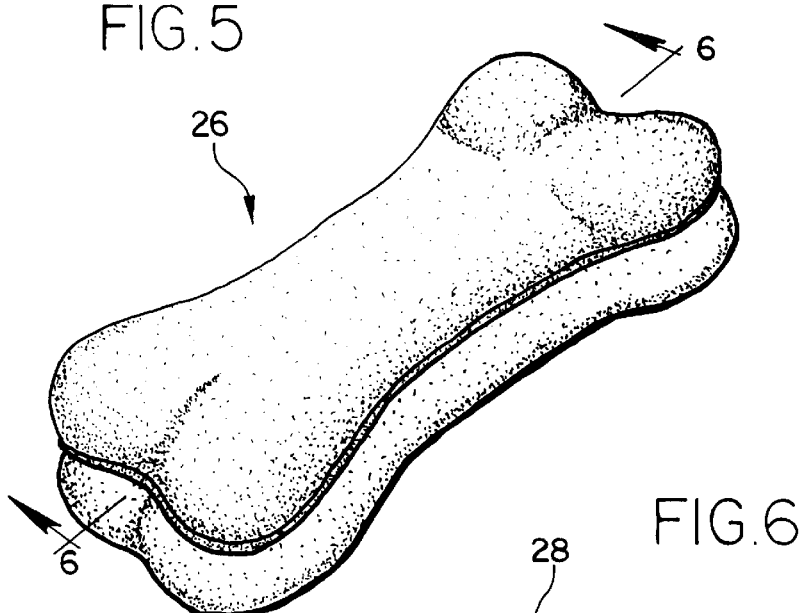
FIG. 5 is a perspective view of a sandwich dog biscuit.
Figure 6:
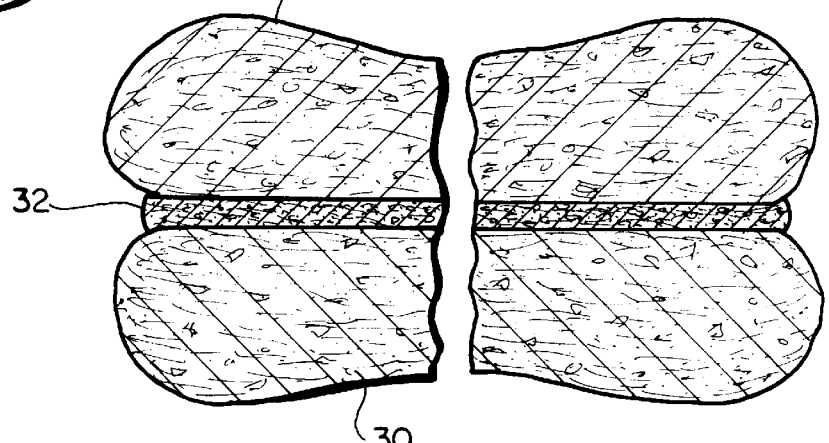
FIG. 6 is a cross-sectional view of the biscuit in FIG. 5 taken along line 6—6 of FIG. 5.

Reference to FIGS. 5 and 6 illustrate a sandwich pet foodstuff 26, which in this case is a dog biscuit, in accordance with the invention. Sandwich pet foodstuff 26 is composed of a solid body 28 and solid body 30, both of baked farinaceous material, held together in substantial registry by a xylitol-containing filling or layer 32. Body 28 and body 30 of sandwich pet foodstuff 26 can be made in a manner similar to that used to produce body 12 in FIGS. 1 and 2. Xylitol filling 32 consists of xylitol, gum arabic and other ingredients and functions to permanently bind or adhere together bodies 28 and 30 when layer 32 is substantially dried or cured.

Figure 7:
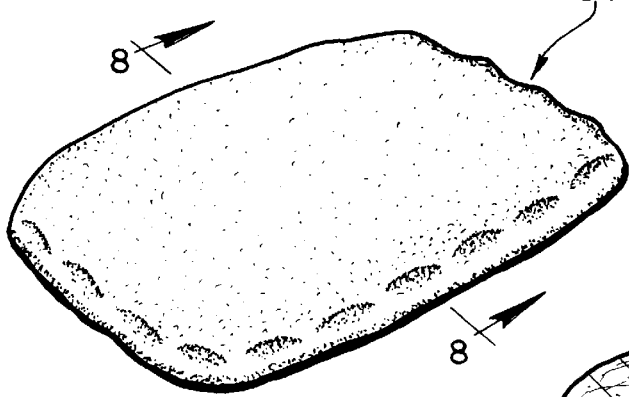
FIG. 7 is a perspective view of a pocket dog biscuit.
Figure 8:
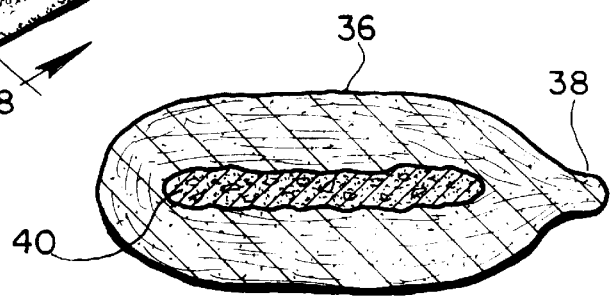
FIG. 8 is a cross-sectional view of the biscuit in FIG. 7 taken along line 8—8 of FIG. 7.

Reference to FIGS. 7 and 8 illustrate a pocket pet foodstuff 34, which in this case is a dog biscuit, in accordance with the invention. Pocket pet foodstuff 34 is composed of a solid body 36 of baked farinaceous material, crimped on edges 38 around an enclosed xylitol center 40. Body 36 of pocket pet foodstuff 34 can be made in a manner similar to that used to produce body 12 in FIGS. 1 and 2. Xylitol-containing layer 32 consists of xylitol, lactitol and other ingredients.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

What is claimed is:

1. A method of using a water soluble consumable mouthwash powder comprising an effective amount of xylitol to reduce the incidence of dental caries in non-human animals, comprising the steps of adding the mouthwash powder to water; mixing the solution; and placing the solution for the pet to drink.

2. A method of reducing the incidence of dental caries in non-human animals by orally administering an effective amount of xylitol.

3. A method of reducing the incidence of dental plaque or tartar in non-human animals by orally administering an effective amount of xylitol.

4. A topical gel toothpaste comprising essentially of a mixture of xylitol, lactitol and hydrogenated starch hydrolyzate syrup in an effective amount for dental caries prevention in non-human animals.

5. An edible pet foodstuff for reducing the incidence of caries comprising a hard solid edible body having xylitol dispersed in the solid body in an amount effective to reduce the incidence of dental caries when chewed by a pet so that when the food is chewed by a pet, the solid body breaks into smaller pieces and scrapes at built-up plaque and the xylitol comes into contact with the pet's teeth and gums to reduce the incidence of dental caries.

6. The foodstuff of claim 5 wherein the xylitol is present in an amount of from about 0.25% to about 2.5% by total weight of the foodstuff.

7. The foodstuff of claim 5 further comprising a coating comprising xylitol on the exterior of the solid body.

* * * * *